United States Patent
Will et al.

(10) Patent No.: US 11,557,381 B2
(45) Date of Patent: Jan. 17, 2023

(54) CLINICAL TRIAL EDITING USING MACHINE LEARNING

(71) Applicant: International Business Machines Corporation, Armonk, NY (US)

(72) Inventors: Eric W Will, Rochester, MN (US); Adam Clark, Mantorville, MN (US); Kimberly Diane Kenna, Cary, NC (US)

(73) Assignee: MERATIVE US L.P., Ann Arbor, MI (US)

( * ) Notice: Subject to any disclaimer, the term of this patent is extended or adjusted under 35 U.S.C. 154(b) by 119 days.

(21) Appl. No.: 16/283,891

(22) Filed: Feb. 25, 2019

(65) Prior Publication Data
US 2020/0273547 A1 Aug. 27, 2020

(51) Int. Cl.
*G16H 10/20* (2018.01)
*G06N 20/00* (2019.01)
(Continued)

(52) U.S. Cl.
CPC .......... *G16H 10/20* (2018.01); *G06F 40/205* (2020.01); *G06F 40/30* (2020.01); *G06N 20/00* (2019.01)

(58) Field of Classification Search
CPC .. G06Q 50/22–24; G16H 10/20; G06F 19/30; G06F 19/32; G06F 19/34;
(Continued)

(56) References Cited

U.S. PATENT DOCUMENTS 7,054,823 B1 * 5/2006 Briegs ............... G06F 19/36
705/2
7,730,467 B1 * 6/2010 Hejlsberg ............ G06F 40/221
717/142

(Continued)

FOREIGN PATENT DOCUMENTS

EP 3376400 A1 * 9/2018 ............ G06N 5/022
WO WO-9927432 A2 * 6/1999 ....... G06F 17/30569
(Continued)

OTHER PUBLICATIONS

S.B. Kotsiantis, "Supervised Machine Learning: A Review of Classification Techniques", 2007, Informatica, 31, 249-268, all pages, http://www.informatica.si/index.php/informatica/article/viewFile/148/140 (Year: 2007).*

(Continued)

*Primary Examiner* — Jason S Tiedeman
*Assistant Examiner* — Jessica Marie Webb
(74) *Attorney, Agent, or Firm* — Patterson + Sheridan, LLP (57) ABSTRACT

Methods and apparatuses for performing clinical trial editing using machine learning are provided. One example method generally includes receiving information of a first clinical trial that is being drafted and identifying, in a corpus of literature, a plurality of documents that are relevant to the first clinical trial, based on the title of the first clinical trial. The method further includes providing the plurality of documents and the plurality of criteria to a machine learning model configured to output for each respective criterion of the plurality of criteria, a confidence value for the respective criterion, receiving as output from the machine learning model the confidence value for each respective criterion and, upon determining that a first criterion has a first confidence (Continued)

value below a predefined threshold, prompting a user to verify the first criterion.

18 Claims, 4 Drawing Sheets

(51) Int. Cl.
  *G06F 40/30* (2020.01)
  *G06F 40/205* (2020.01)
(58) Field of Classification Search
  CPC ...... G06F 19/36; G06F 40/205; G06F 40/211; G06F 40/216; G06F 40/221; G06F 40/226; G06F 40/30; G06F 40/35; G06N 20/00; G06N 20/10; G06N 20/20
  See application file for complete search history.

(56) References Cited

U.S. PATENT DOCUMENTS

| | | | | |
|---|---|---|---|---|
| 8,065,347 | B1* | 11/2011 | DeMeyer | G06F 16/217 707/806 |
| 9,754,083 | B2 | 9/2017 | Kleeman et al. | |
| 10,083,161 | B2* | 9/2018 | Freed | G16H 50/20 |
| 10,140,421 | B1* | 11/2018 | Bernard | G06F 40/30 |
| 10,832,146 | B2* | 11/2020 | Kaufmann | G06N 20/20 |
| 11,024,406 | B2* | 6/2021 | Sadeghi | G16H 15/00 |
| 2004/0249664 | A1* | 12/2004 | Broverman | G16H 10/20 705/2 |
| 2008/0091634 | A1* | 4/2008 | Seeman | G06N 5/022 706/59 |
| 2009/0276438 | A1* | 11/2009 | Lake | G06F 16/242 |
| 2009/0313048 | A1* | 12/2009 | Kahn | G16H 15/00 705/3 |
| 2012/0259647 | A1* | 10/2012 | Syed | G16H 10/20 705/2 |
| 2013/0132112 | A1* | 5/2013 | Sablinski | G16H 70/60 705/2 |
| 2014/0122113 | A1 | 5/2014 | Hoffman, Jr. et al. | |
| 2014/0280210 | A1* | 9/2014 | Ritchie | G06F 40/205 707/748 |
| 2015/0120725 | A1* | 4/2015 | de Vries | G16H 10/20 707/736 |
| 2016/0125171 | A1* | 5/2016 | Finken | G06F 16/245 705/2 |
| 2016/0196389 | A1* | 7/2016 | Moturu | G16H 50/20 705/2 |
| 2016/0246945 | A1* | 8/2016 | Allen | G16H 20/40 |
| 2016/0256945 | A1* | 9/2016 | Goto | B23H 3/08 |
| 2017/0076046 | A1* | 3/2017 | Barnes | G16H 30/20 |
| 2017/0124291 | A1 | 5/2017 | Barken | |
| 2018/0046780 | A1* | 2/2018 | Graiver | G06F 40/44 |
| 2018/0101598 | A1* | 4/2018 | Allen | G06F 40/268 |
| 2018/0122509 | A1* | 5/2018 | Christiansson | G16H 10/60 |
| 2018/0261333 | A1* | 9/2018 | Balsz | G16H 20/70 |
| 2018/0300315 | A1* | 10/2018 | Leal | G06F 16/355 |
| 2020/0073940 | A1* | 3/2020 | Grosset | G06F 40/30 |
| 2020/0159829 | A1* | 5/2020 | Zhao | G06T 11/206 |
| 2020/0218779 | A1* | 7/2020 | Stevens | G16H 10/20 |
| 2020/0250209 | A1* | 8/2020 | Chakrapani | G16H 15/00 |

FOREIGN PATENT DOCUMENTS

| | | | | |
|---|---|---|---|---|
| WO | WO-2014197635 | A2 * | 12/2014 | ......... G06F 16/2457 |
| WO | 2015157235 | A1 | 10/2015 | |

OTHER PUBLICATIONS

Ricky Ho. (2012). Characteristics of Machine Learning Model. Blogger, all pages, horicky.blogspot.com/2012/02/characteristics-of-machine-learning.html (Year: 2012).*

Rabelo et al., "Development of a real-time learning scheduler using reinforcement learning concepts," Proceedings of 1994 9th IEEE International Symposium on Intelligent Control, Columbus, OH, USA, 1994, pp. 291-296. (Year: 1994).*

Natural language processing. (2008). In D. Crystal, Language library: A dictionary of linguistics and phonetics (6th ed.). Wiley. Credo Reference: https://search.credoreference.com/content/entry/bkdictling/natural_language_processing/0?institutionId=743 (Year: 2008).*

T. Young, D. Hazarika, S. Poria and E. Cambria, "Recent Trends in Deep Learning Based Natural Language Processing [Review Article]," in IEEE Computational Intelligence Magazine, vol. 13, No. 3, pp. 55-75, Aug. 2018, doi: 10.1109/MCI.2018.2840738. (Year: 2018).*

Korkontzelos, I., Mu, T. & Ananiadou, S. Ascot: a text mining-based web-service for efficient search and assisted creation of clinical trials. BMC Med Inform Decis Mak 12, S3 (2012). https://doi.org/10.1186/1472-6947-12-S1-S3 (Year: 2012).*

* cited by examiner

CLINICAL TRIAL EDITING USING MACHINE LEARNING

BACKGROUND

The present invention relates to authoring clinical trials, and more specifically, to editing clinical trials using machine learning techniques.

Clinical trials are used by researchers to test new therapies for medical uses. Such clinical trials typically include criteria, whether explicit or implicit, related to the types of patients suitable for the trial, including various patient attributes such as age of the patient or medical conditions of the patient.

Unfortunately, clinical trials are often described in complex documents, which may have sections written by different authors and/or at different times. In many cases, clinical trial documents, or portions thereof, from related (but distinct) therapies may be reused by researchers. As a result of these issues, the patient selection criteria of clinical trials can often be confusing, inaccurate, or even contradictory. For example, some criteria may be subject to multiple interpretations or meanings, or criteria in one portion of a clinical trial document may be inconsistent with criteria in another portion of the clinical trial document.

Currently, the only method of correcting the criteria of clinical trial documents is manual inspection of clinical trial documents to identify the criteria, followed by manual analysis of the criteria to determine the usefulness, necessity, and relevance of the criteria to the clinical trial. Manual identification and analysis is time-consuming, inefficient and may miss some issues with the criteria, especially criteria with multiple meanings. Therefore, systems and methods are needed to automate the analysis of clinical trial criteria.

SUMMARY

Certain embodiments provide a method for clinical trial editing using machine learning. The method generally includes receiving information of a first clinical trial that is being drafted, wherein the information includes a plurality of criteria for the first clinical trial and a title of the first clinical trial and identifying, in a corpus of literature, a plurality of documents that are relevant to the first clinical trial, based on the title of the first clinical trial. The method further includes providing the plurality of documents and the plurality of criteria to a machine learning model configured to output for each respective criterion of the plurality of criteria, a confidence value for the respective criterion, receiving as output from the machine learning model the confidence value for each respective criterion and, upon determining that a first criterion has a first confidence value below a predefined threshold, prompting a user to verify the first criterion.

Some embodiments of the method for clinical trial editing further include determining that a second criterion of the plurality of criteria has two potential meanings, generating a plurality of alternative criteria for the second criterion, and presenting the plurality of alternative criteria to the user. Other embodiments of the method for clinical trial editing further include determining at least one criterion is present in related trials but not the criteria of the first clinical trial and generating a new criteria, wherein the new criteria is not included in the plurality of criteria.

Another embodiment includes a computing device comprising a processor and memory including instructions that cause the computing device to perform the method for clinical trial editing using machine learning described above. Still another embodiment includes non-transitory computer readable medium comprising instructions, which when executed by a processor of a computing device, cause the computing device to perform the method for clinical trial editing using machine learning described above.

DETAILED DESCRIPTION

In order to perform automated analysis of clinical trial documents, a method employing machine learning techniques may be employed. In general, a trial editing service may generate a searchable trial index by accessing a repository of clinical trial documents and other therapy-related documents. The trial editing service can then receive a request to perform analysis of a particular clinical trial from a user of the trial editing service, which may be a researcher or other author of a clinical trial. Using the title of the clinical trial, the trial editing service can identify related documents within the trial index.

Upon identifying the related documents, the trial editing service can extract criteria of the clinical trial and compare the extracted criteria to attributes of the related documents. Using this comparison, the trial editing service can identify potential problems within the clinical trial, such as contradictory criteria, criteria with multiple meanings, or criteria that are not relevant to the therapeutic subject of the clinical trial.

Based on the above comparison, the trial editing service can provide various pieces of information to the user, such as an elaboration of problems with the criteria as written, or suggestions for alternate or additional criteria that may improve documents describing the clinical trial. In some cases, the trial editing service may prompt the user to verify that a particular criterion is accurate as written.

For illustration, consider the following non-limiting example: a researcher is authoring a clinical trial in order to study the effectiveness of a new medication, and the researcher has reused some material from a related clinical trial for a different medication. The reused material includes a criterion limiting clinical trial patients to a certain age range. By comparing clinical trial information to related documents, a trial editing service identifies potential issues with the clinical trial as currently drafted. In this example, the related documents do not include limitations of patients to a particular age range, and thus the trial editing service determines that the criterion may be inaccurate. The trial editing service can then prompt the researcher to confirm if that criterion is indeed valid for studying the new medication.

Using the above described method, various advantages over existing clinical trial editing techniques may be realized. In particular, the above described method can be used to automate clinical trial editing, which allows for greater accuracy, efficiency, and speed than is possible in current manual methods of clinical trial editing. Further, the above described method can be used to identify clinical trial issues that may be difficult to manually identify by authors of clinical trials, such as conflicting information in different parts of a clinical trial, or criteria of the clinical trial being subject to multiple meanings.

Figure 1:
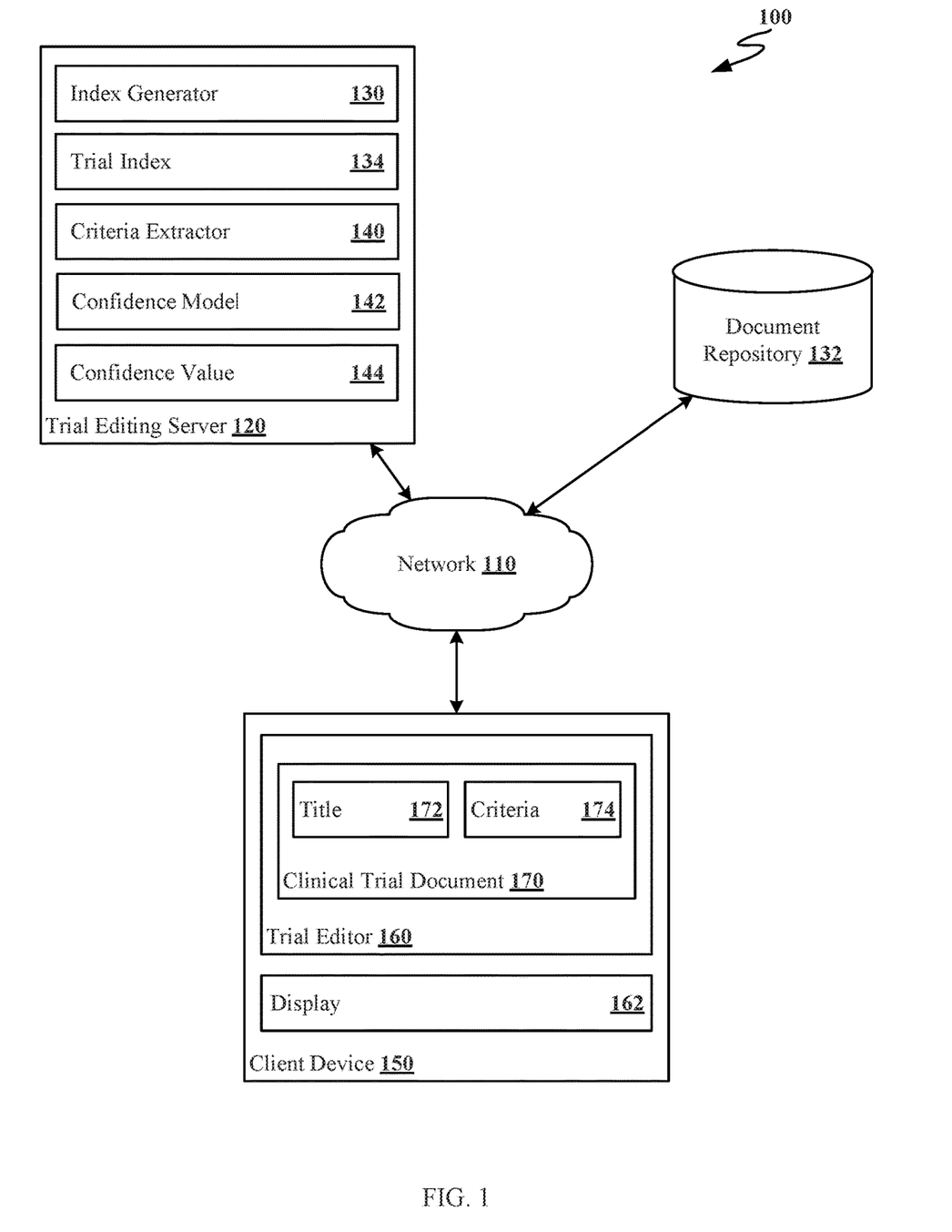
FIG. 1 depicts an example computing environment for performing clinical trial editing using machine learning.

FIG. 1 depicts an example computing environment 100 for performing clinical trial editing using machine learning. Computing environment 100 includes trial editing server 120, document repository 132 and client device 150 connected via network 110. However, in other embodiments, the functions of trial editing server 120, client device 150 and document repository 132 may be performed by a single device, or by a number of additional devices interconnected, such as in a cloud computing environment. Further, in other examples document repository 132 may be connected to trial editing server 120 or may be a storage device of trial editing server 120, rather than available to trial editing server 120 via network 110.

Trial editing server 120 is a computing device including at least one processor and at least one memory (not shown). Trial editing server 120 includes various data files and software routines that collectively constitute a trial editing service. In this example, trial editing server 120 includes index generator 130, trial index 134, criteria extractor 140, confidence model 142, and confidence value 144.

Index generator 130 is a software routine executing on trial editing server 120 used to generate trial index 134. Trial index 134 is a file used by the trial editing service to compare a given clinical trial with other related clinical trials. In some cases, trial index 134 may be a vector space including vectors associated with particular documents, with similar documents clustered together.

In general, index generator 130 accesses document repository 132 in order to generate trial index 134. Document repository 132 is a repository, database, or other storage device used to store a plurality of medical documents, such as clinical trial documents. In some examples, the functions of document repository 132 may be performed by a cloud storage device. In this example, the documents stored within document repository 132 include at least some portion of natural language text.

Index generator 130 utilizes one or more natural language processing (NLP) techniques to identify characteristics of documents included in the document repository 132. In some cases, NLP may include various preprocessing tasks on the text of the documents. Such preprocessing tasks include removing stop words, performing tokenization, performing stemming, removing non-English words or removing punctuation. Index generator 130 may generate vectors for each document, and plot those vectors within trial index 134.

Index generator 130 may analyze predefined sections of the documents, such as sections identified by headings or by metadata tags, and only parses the rest of a document if the specified section(s) cannot be found or do not exist in the document. In some embodiments, index generator 130 also remedies unknown terms in the documents, such as through disambiguation and acronym resolution. For example, if a document includes an acronym, in one embodiment, index generator 130 can expand the acronym. Index generator 130 may periodically update trial index 134, such as if new documents have been added to document repository 132.

Index generator 130 then categorizes, or clusters, related documents together, such as by use of a clustering algorithm.

If the documents are clinical trial documents, index generator 130 may use identified criteria of the clinical trial documents to organize them according to their criteria. Index generator 130 may also use titles of the documents to categorize the documents. Using any suitable clustering algorithm, index generator 130 identifies clusters of related vectors, which correspond to related documents.

After trial index 134 has been generated and/or updated, trial index 134 can be used in analyzing clinical trials. In this example, data of the clinical trial is obtained from client device 150.

Client device 150 is a computing device including at least one processor and at least one memory (not shown). Client device 150 further includes at least one display 162, such as a screen. Client device 150 is used to execute trial editor 160, a locally-executing client application of the trial editing service. In other examples, client device 150 may be the execution device for the entirety of the trial editing service, rather than running in a client-server model. In such a case, trial editor 160 may perform the functions performed by trial editing server 120.

In this example, trial editor 160 includes a single clinical trial document 170. A user of client device 150 (such as a researcher or other clinical trial author) is using trial editor 160 to draft clinical trial document 170. Clinical trial document 170 is a file defining a clinical trial for use in studying or testing a particular therapy, such as a medication or medical technique. Clinical trial document 170 includes a title 172 and a plurality of criteria 174. Criteria 174 define the limitations for potential patients in studying the therapy. Although shown as a distinct entity for simplicity, in most clinical trials, the criteria of the clinical trial may be defined throughout a clinical trial document.

While the user of client device 150 is drafting clinical trial document 170 information of clinical trial document 170 may be transmitted to trial editing server 120 for analysis. In some examples, the user may request analysis of clinical trial document 170, while in other examples trial editor 160 may periodically send clinical trial information to the trial editing server 120 for proactive analysis.

In this example, upon receipt of information of clinical trial document 170, the trial editing service uses title 172 to search for documents related to clinical trial document 170 within trial index 134. Such search may involve comparing a vector of title 172 to the vector space of trial index 134, and identifying a related document or a cluster of related documents relevant to title 172.

After the related documents have been located, criteria extractor 140 identifies and extracts criteria 174 from clinical trial document 170. In this example, criteria extractor 140 is a software routine executing on trial editing server 120. Criteria extractor 140 makes use of various NLP techniques to identify criteria 174 of the clinical trial. In some examples, criteria extractor 140 may generate a vector representation of each criterion of criteria 174 in order to prepare criteria 174 for analysis.

Once criteria 174 have been extracted, criteria 174 may be provided to confidence model 142 as input. In this example, confidence model 142 is a machine learning model executing on trial editing server 120. Although executing on trial editing server 120, confidence model 142 may be trained on a separate computing device, such as a dedicated training server (not shown). Confidence model 142 accepts clinical trial criteria as input and produces a confidence value 144 as output for each criterion provided as input. Confidence value 144 is a data point stored in memory of trial editing server 120, representing the confidence, in terms accuracy, relevance and usefulness, for a particular criterion. Although confidence value 144 may be scaled using any arbitrary scaling values, for simplicity confidence values scaled from 0 to 100 are used herein.

Confidence value 144 may be based on a comparison of criteria 174 to comparison criteria of the related documents as previously identified. For example, if a criterion of criteria 174 does not appear in any of the comparison criteria, confidence model 142 may produce a low confidence value for the criterion. In addition, different documents may be given more or less weight when used to analyze criteria 174. For example, comparison criteria obtained from successful clinical trials may be given more weight than comparison criteria obtained from unsuccessful clinical trials.

After producing confidence values for each criterion of criteria 174, the trial editing service compares the confidence values against a confidence threshold. Criterion whose respective confidence values fall below the confidence threshold may be presented to the user to verify the inclusion of that criterion. For example, if confidence values are scaled from 0 to 100, criteria whose confidence values are 50 or below may be presented to the user for verification. Note that the exact value of the confidence threshold may vary in different implementations of the methods described herein.

In other examples, the trial editing service may perform additional analysis using the information of clinical trial document 170. For example, an additional machine learning model (not shown) may be used to identify likely additional criteria 174. For example, if most related documents of clinical trial document 170 include a particular criterion that is not included in criteria 174, the trial editing service may suggest the particular criterion as an addition to criteria 174.

In still other examples, the trial editing service may suggest alternate criteria when analysis of a criterion of criteria 174 indicates the criterion is subject to multiple meanings. In such a case, the trial editing service may generate two criteria, each corresponding to one meaning of the criterion, and provide the two criteria to the user, with a suggestion that one of the two criteria may be more accurate than the criteria would be.

The trial editing service may also generate and analyze a logical graph of criteria 174, in order to identify potential logical issues with criteria 174, such as contradictions. For example, if clinical trial document 170 initially limits patient age range to patients over 60, this is added as a criterion in criteria 174. If clinical trial document 170 later limits the patient age range to patients under 45, this is also added as a criterion in criteria 174. Thereafter, upon analysis of the logical graph of criteria 174, the trial editing service can identify the logical contradiction between the two criteria above. Although age range is used as an example for simplicity, other types of contradictions are possible, such as requiring and prohibiting certain medical conditions or medications.

In general, upon determining a criterion falls below the confidence threshold for any reason, the trial editing service can prompt the user of client device 150 for verifications, or can present information or explanations to the user via client device 150. In such cases, a graphical user interface of trial editor 160 may be displayed to the user via display 162. The user may be able to interact with the graphical user interface in order to respond to prompts from the trial editing service, or to implement suggestions from the trial editing service into clinical trial document 170.

Figure 2:
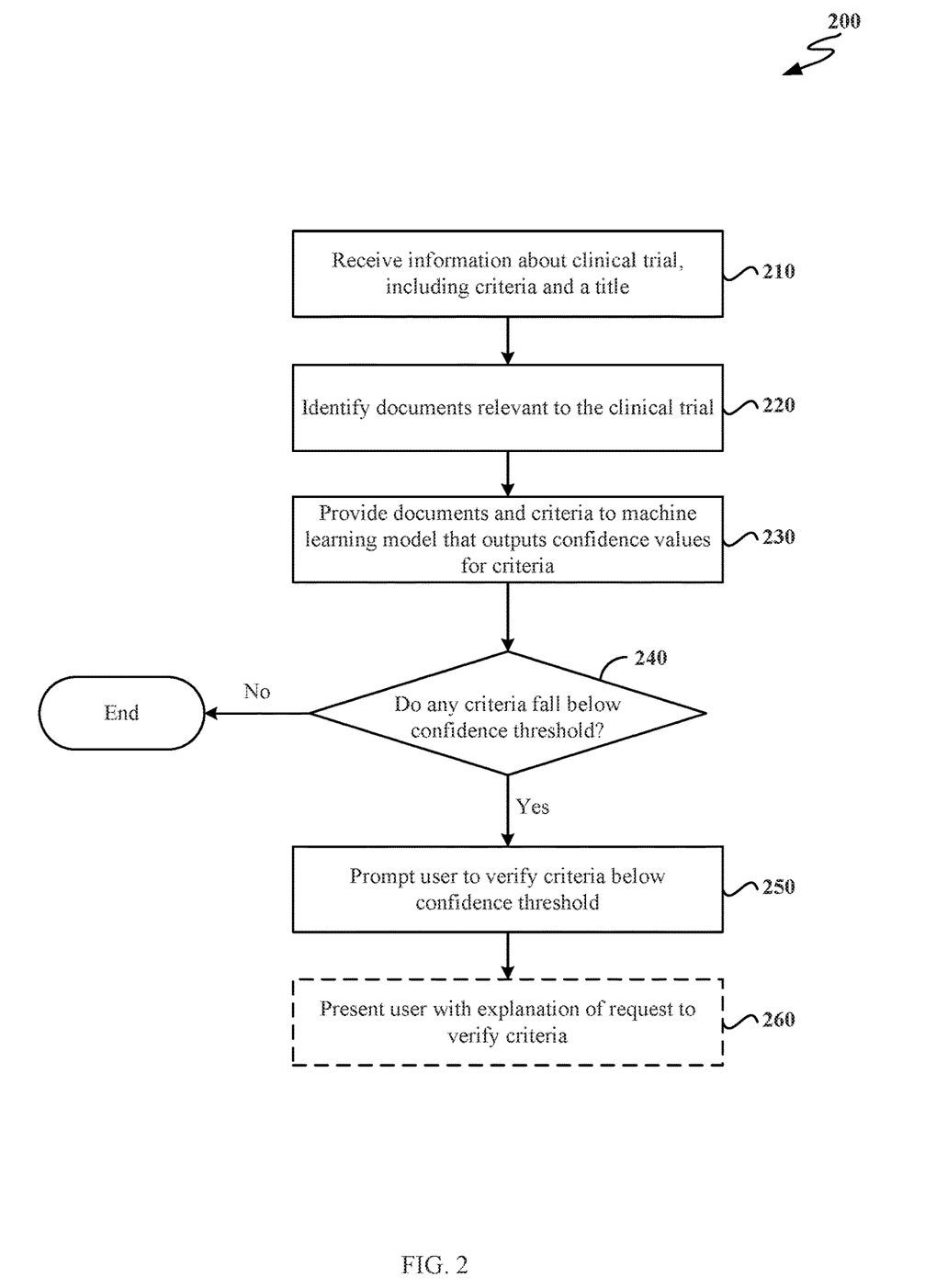
FIG. 2 is a flow chart of an example method for performing clinical trial editing using machine learning.

FIG. 2 is a flow chart of an example method 200 for performing clinical trial editing using machine learning. Method 200 may be performed by a trial editing server, such as trial editing server 120 of FIG. 1.

Method 200 begins at 210, where the trial editing server receives information of a first clinical trial, wherein the information includes a plurality of criteria for the first clinical trial and a title of the first clinical trial. As described above, the information of the first clinical trial may be received from a client device executing a locally-executing client application, such as client device 150 of FIG. 1. The information of the first clinical trial may be received by the trial editing server for a number of reasons, including as part of an explicit request by a user of the client device to analyze or edit a clinical trial document.

At 220, the trial editing server identifies, in a corpus of literature, a plurality of documents that are relevant to the first clinical trial, based on the title of the first clinical trial. In some cases, this may involve using the title of the first clinical trial to identify a cluster of vectors (or other data points) in a trial index related to the first clinical trial, where the data points are each associated with a particular document. Collectively, the documents associated with the data points are the plurality of documents.

At 230, the trial editing server provides the plurality of documents and the plurality of criteria to a machine learning model configured to output for each respective criterion of the plurality of criteria, a confidence value for the respective criterion. A confidence value for a criterion represents the estimated probability that the criterion is relevant to or accurate for the first clinical trial.

At 240 the trial editing server determines if any of the confidence values for the criteria fall below a confidence threshold. The exact confidence threshold used may vary, and may be dependent on the scaling used for the confidence values. However, in general, the confidence threshold used can be adjusted to more closely or less closely scrutinize criteria in different contexts. For example, clinical trials in a relatively new therapeutic area may be less closely scrutinized (e.g., criteria for such clinical trials is measured against a lower confidence threshold) than clinical trials in more established therapeutic areas. If no confidence values fall below the confidence threshold, method 200 ends. If at least one confidence value falls below the confidence threshold, method 200 proceeds to 250.

At 250, the trial editing server prompts the user to verify criteria whose confidence values fell below the confidence threshold, as determined at 240. Such prompting may be performed in many ways, such as by displaying information in a graphical user interface on a display of the client device. Prompting may also include emails, push notifications, or other transmissions intended for the user, depending on the type of computing device used by the user. The user's response to the prompting may be used to update the machine learning model used to calculate the confidence values. For example, if the user verifies that a criterion prompted by the trial editing server is correct, the machine learning model may be updated to produce higher confidence values for criterion similar to the verified criterion.

In some examples, method 200 further includes 260. At 260, the trial editing server presents the user with an explanation of the request to verify criteria of 250. Such explanation may include different information depending on the nature of the low confidence value for the criterion that resulted in prompting. For example, if the low confidence value was based on infrequency of the criterion compared to criteria of related documents, the frequency rate in the related documents, as well as an identification of the category of related documents, may be provided. If the low confidence value was based on a contradiction of the criteria, the contradictory criteria may be presented to the user with an explanation of the logical conflict.

In some examples of method 200, analyzing the plurality of documents to determine the confidence value for the respective criterion comprises determining a relevancy of the respective criterion with respect to each of the plurality of documents. Relevancy may be determined based on frequency of criterion occurrence in the plurality of documents or a similarity of the criterion to terms in the plurality of documents. For example, if the criterion specifies patients with a particular medical condition, relevancy may be determined based on the frequency of occurrence of that medical condition in the plurality of documents, or the sequence of occurrence of similar terms (e.g., related medical conditions) in the plurality of documents.

For some embodiments of method 200, the information of the first clinical trial further includes a domain of the first clinical trial. Further, identifying the plurality of documents may be further based on the domain of the first clinical trial. Examples of domains include a therapeutic area of a clinical trial, a particular family of diseases or disorders or any other categorization of clinical trials.

Some examples of method 200 further include estimating a first number of patients that are eligible for the first clinical trial based on the plurality of criteria. Such examples also may include estimating a second number of patients that are eligible for the first clinical trial based on all of the plurality of criteria other than the first criterion and presenting the first and second numbers to the user. This information allows the user to easily ascertain the effect the presence of the first criterion has on the number of potential patients for the first clinical trial. For example, a criteria may be accurate for a clinical trial, but may result in a restricted number of potential patients such that exclusion of the criteria may nonetheless be appropriate.

In some cases determining the confidence value for the first criterion comprises determining that the first criterion contradicts itself. In other cases, determining the confidence value for the first criterion comprises determining that a second criterion contradicts the first criterion.

Figure 3A:
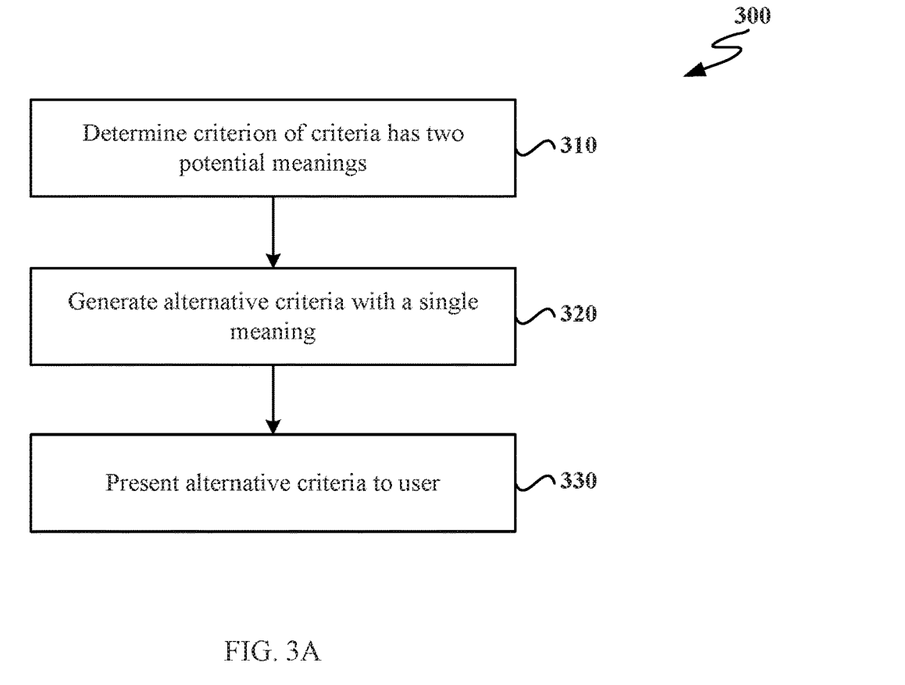
FIG. 3A is a flow chart of an example method for preparing alternative criteria to present to a user.

FIG. 3A is a flow chart of an example method 300 for preparing alternative criteria to present to a user. Method 300 may be performed by a trial editing server, such as trial editing server 120 of FIG. 1. Method 300 is a continuation or extension of method 200 of FIG. 2.

Method 300 begins at 310, where the trial editing server determines that a second criterion of the plurality of criteria has two potential meanings. Such a determination may be made by the trial editing server based on parsing the second criterion with one or more NLP models. For example, an NLP model configured to output a probability that a criterion has a particular meaning may output two relatively similar probabilities for two meanings of the second criterion, (meaning the NLP model does not have a high degree of confidence in either meaning). In other examples, one NLP model may output a first meaning for the second criterion while a second NLP model outputs a second meaning for the second criterion.

At 320, the trial editing server generates a plurality of alternative criteria for the second criterion, wherein each of the plurality of alternative criteria has a single respective meaning. The plurality of alternative criteria may be based on a frequency or relevancy (as discussed above) of the alternative criteria to the plurality of documents.

At 330, the trial editing server presents the plurality of alternative criteria to the user. Presenting the plurality of alternative criteria may take a variety of forms, such as displaying the alternative criteria to the user via a screen or other display of the client device used by the user.

Figure 3B:
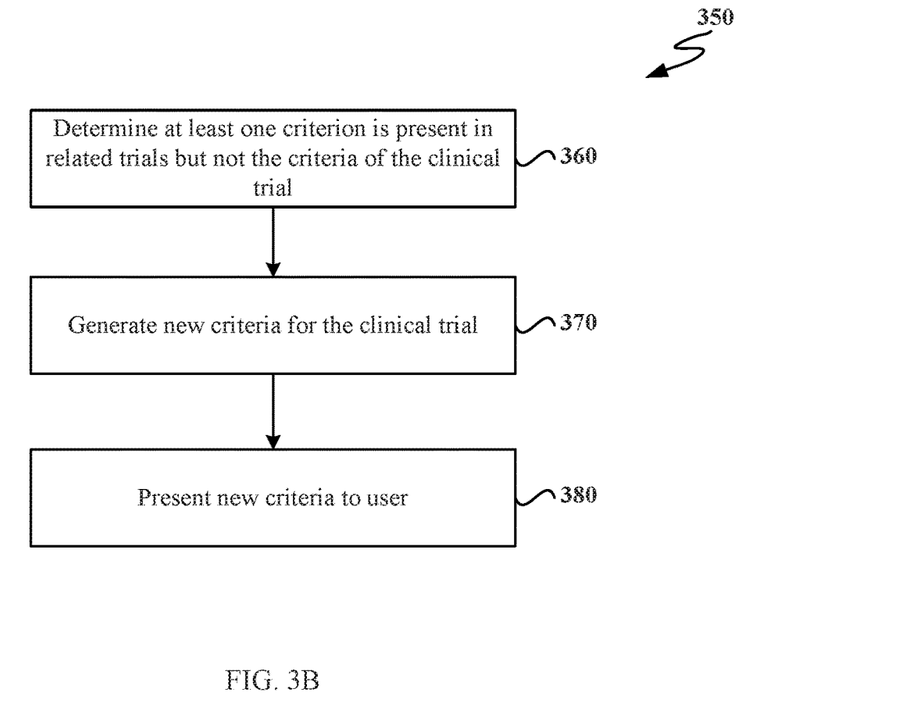
FIG. 3B is a flow chart of an example method for preparing new criteria to present to a user.

FIG. 3B is a flow chart of an example method 350 for preparing new criteria to present to a user. Method 350 may be performed by a trial editing server, such as trial editing server 120 of FIG. 1. Method 350 is a continuation or extension of method 200 of FIG. 2.

Method 350 begins at 360, where the trial editing server determines at least one criterion is present in related trials but not the criteria of the first clinical trial. This determination may be based on analyzing the plurality of documents, to establish a frequency of occurrence for the at least one criterion across the plurality of documents (e.g., if there are 100 documents in the plurality of documents, how many of those 100 documents include the at least one criterion). In some cases, documents associated with successful clinical trials may be given increased weight to identify criteria that were unique to the successful clinical trials. Success of a clinical trial may be measured by multiple standards, such as the therapy of the clinical trial obtaining regulatory approval, or the therapy of the clinical trial passing a minimum threshold of successful treatment of a medical condition.

At 370, the trial editing server generates a new criteria, wherein the new criteria is not included in the plurality of criteria. In general, the new criteria may correspond to a limitation for patient selection in the first clinical trial that may improve the chances of successful performance of the first clinical trial. For example, the author of the first clinical trial may have inadvertently omitted a patient selection criteria important to the study.

At 380, the trial editing server presents the new criteria to the user, such as using the methods for presentation or prompting discussed above.

Figure 4:
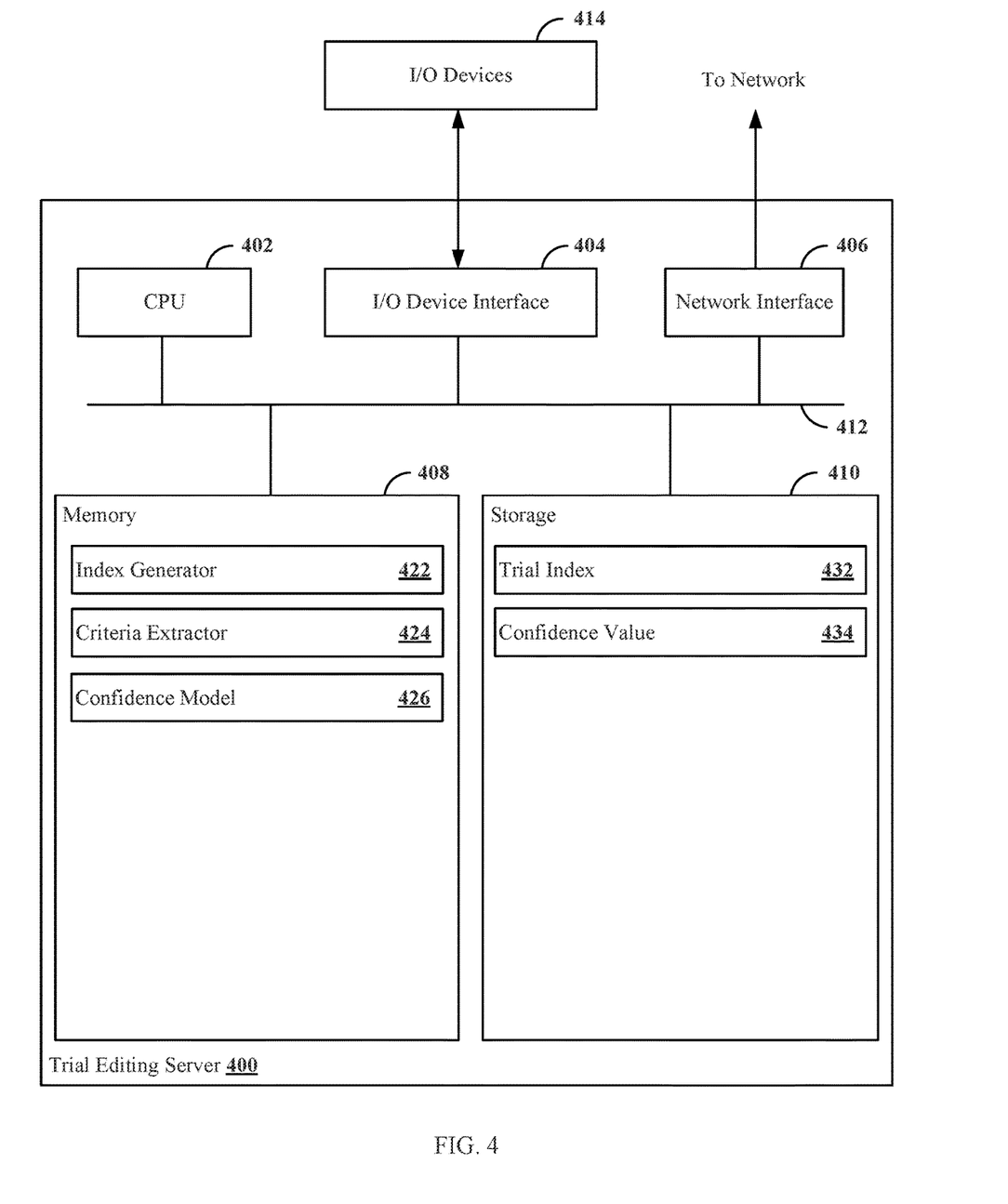
FIG. 4 is a block diagram of an example trial editing server.

FIG. 4 is a block diagram of an example trial editing server 400. As shown, trial editing server 400 includes a central processing unit (CPU) 402, one or more input/output (I/O) device interfaces 404, which may allow for the connection of various I/O devices 414 (e.g., keyboards, displays, mouse devices, pen input, etc.) to the trial editing server 400. Trial editing server 400 also includes network interface 406, memory 408, storage 410, and interconnect 412.

CPU 402 may retrieve and execute programming instructions stored in memory 408. Similarly, CPU 402 may retrieve and store application data residing in memory 408. Interconnect 412 allows for transmission of programming instructions and application data, among CPU 402, I/O device interface 404, network interface 406, memory 408, and storage 410. CPU 402 is included to be representative of a single CPU, multiple CPUs, a single CPU having multiple processing cores, and the like.

I/O device interface 404 may provide an interface for capturing data from one or more input devices integrated into or connected to trial editing server 400, such as keyboards, mice, touchscreens, and so on. Memory 408 may represent a random access memory (RAM), while storage 410 may be a solid state drive, for example. Although shown as a single unit, storage 410 may be a combination of fixed and/or removable storage devices, such as fixed drives, removable memory cards, network attached storage (NAS), or cloud-based storage.

As shown, memory 408 includes index generator 422, criteria extractor 424 and confidence model 426. Index generator 422, criteria extractor 424 and confidence model 426 are software routines executed based on instructions which may be stored in the storage 410. Such instructions may be executed by the CPU 402.

As shown, storage 410 includes trial index 432 and confidence value 434. In general, index generator 422 generates trial index 432 using a repository of documents, such as a repository accessible via network interface 406. Thereafter, trial editing server 400 receives information of a first clinical trial, such as from a client device, also via network interface 406. Criteria extractor 424 then extracts criteria of the first clinical trial, and passes at least one criterion of the criteria of the first clinical trial to confidence model 426. Confidence model 426 produces confidence value 434 as output. Trial editing server 400 may thereafter prompt a user of the client device regarding the at least one criterion, based on confidence value 434.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications of the trial editing service or related data available in the cloud. For example, the functions of the trial editing server could be executed on a computing system in the cloud to analyze clinical trial documents. In such a case, the trial editing service could receive information of a clinical trial, produce confidence values for the clinical trial and store the confidence values at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A computer implemented method comprising:
   generating, by operation of one or more computer processors, an index for a corpus of literature, wherein the index comprises a vector space comprising a plurality of vectors associated with documents clustered based on similarities, and wherein the index is generated by:
      preprocessing a first document of a plurality of documents using one or more natural language processing (NLP) algorithms, comprising removing stop words, performing tokenization, performing stemming, removing non-English words, and removing punctuation;
      identifying a first instance of a predefined section of the first document based on metadata tags associated with the first document;
      generating a first vector based on characteristics of the first document, comprising:
         parsing only the first instance of the predefined section; and
         refraining from parsing at least one other section of the first document;
      generating a second vector based on characteristics of a second document, comprising:
         searching for a second instance of the predefined section of the second document; and
         in response to determining the second predefined section cannot be found in the second document, parsing the second document; and
      clustering the first and second documents based on a similarity between the first and second vectors;
   receiving information of a first clinical trial that is being drafted, wherein the information includes a plurality of criteria for the first clinical trial and a title of the first clinical trial;
   generating a first vector for the title of the first clinical trial;
   identifying, based on the index for the corpus of literature, a set of documents that are related to the first clinical trial, based on the first vector and the respective vectors of the plurality of documents in the corpus of literature;
   generating, for each respective criterion of the plurality of criteria, a respective confidence value by providing the respective criterion to a machine learning model trained to output confidence values based on input criteria, wherein the respective confidence value is based at least in part on:
      a respective frequency of the respective criterion in the set of documents, wherein a first document in the set of documents is given increased weight based on determining that the first document is associated with a successful trial of a therapy that obtained regulatory approval;

comparing each respective confidence value with a confidence threshold, wherein the confidence threshold is selected based on scaling used for the confidence values;

upon determining that a first criterion of the plurality of criteria has a first confidence value below the confidence threshold, prompting a user to verify the first criterion;

upon receiving, from the user, verification that the first criterion is correct, updating the machine learning model to produce relatively higher confidence values for criteria that are similar to the first criterion;

determining that a second criterion of the plurality of criteria has two potential meanings, comprising:
  parsing the second criterion with a first natural language processing (NLP) model to generate a first meaning; and
  parsing the second criterion with a second NLP model to generate a second meaning distinct from the first meaning; and generating a plurality of alternative criteria for the second criterion, the plurality of alternative criteria comprising a first alternative criteria having the first meaning and a second alternative criteria having the second meaning.

2. The computer implemented method of claim 1, wherein the machine learning model determines a relevancy of the respective criterion with respect to each of the set of documents.

3. The computer implemented method of claim 1, wherein the information of the first clinical trial further includes a domain of the first clinical trial, and wherein identifying the set of documents is further based on the domain of the first clinical trial.

4. The computer implemented method of claim 1, the method further comprising:
  generating the plurality of alternative criteria for the second criterion, wherein each of the plurality of alternative criteria has a single respective meaning; and
  presenting the plurality of alternative criteria to the user.

5. The computer implemented method of claim 1, the method further comprising:
  generating a new criteria based on analyzing the set of documents, wherein the new criteria is not included in the plurality of criteria; and
  presenting the new criteria to the user.

6. The computer implemented method of claim 1, the method further comprising:
  estimating a first number of patients that are eligible for the first clinical trial based on the plurality of criteria;
  estimating a second number of patients that are eligible for the first clinical trial based on all of the plurality of criteria other than the first criterion; and
  presenting the first number of patients and the second number of patients to the user.

7. The computer implemented method of claim 1, wherein determining the confidence value for the first criterion comprises determining that a second criterion contradicts the first criterion.

8. The computer implemented method of claim 1, further comprising presenting an explanation of the confidence value for the first criterion to the user.

9. A system, comprising:
a processor; and
a memory including computer readable instructions, which, when executed by the processor, cause the system to perform a method comprising:
  generating an index for a corpus of literature, wherein the index comprises a vector space comprising a plurality of vectors associated with documents clustered based on similarities, and wherein the index is generated by:
    preprocessing a first document of a plurality of documents using one or more natural language processing (NLP) algorithms, comprising removing stop words, performing tokenization, performing stemming, removing non-English words, and removing punctuation;
    identifying a first instance of a predefined section of the first document based on metadata tags associated with the first document;
    generating a first vector based on characteristics of the first document, comprising:
      parsing only the first instance of the predefined section; and
      refraining from parsing at least one other section of the first document;
    generating a second vector based on characteristics of a second document, comprising:
      searching for a second instance of the predefined section of the second document; and
      in response to determining the second predefined section cannot be found in the second document, parsing the second document; and
    clustering the first and second documents based on a similarity between the first and second vectors;
  receiving information of a first clinical trial that is being drafted, wherein the information includes a plurality of criteria for the first clinical trial and a title of the first clinical trial;
  generating a first vector for the title of the first clinical trial;
  identifying, based on the index for the corpus of literature, a set of documents that are related to the first clinical trial, based on the first vector and the respective vectors of the plurality of documents in the corpus of literature;
  generating, for each respective criterion of the plurality of criteria, a respective confidence value by providing the respective criterion to a machine learning model trained to output confidence values based on input criteria, wherein the respective confidence value is based at least in part on:
    a respective frequency of the respective criterion in the set of documents, wherein a first document in the set of documents is given increased weight based on determining that the first document is associated with a successful trial of a therapy that obtained regulatory approval;
  comparing each respective confidence value with a confidence threshold, wherein the confidence threshold is selected based on scaling used for the confidence values;
  upon determining that a first criterion of the plurality of criteria has a first confidence value below the confidence threshold, prompting a user to verify the first criterion;
  upon receiving, from the user, verification that the first criterion is correct, updating the machine learning model to produce relatively higher confidence values for criteria that are similar to the first criterion;

determining that a second criterion of the plurality of criteria has two potential meanings, comprising:
parsing the second criterion with a first natural language processing (NLP) model to generate a first meaning; and
parsing the second criterion with a second NLP model to generate a second meaning distinct from the first meaning; and
generating a plurality of alternative criteria for the second criterion, the plurality of alternative criteria comprising a first alternative criteria having the first meaning and a second alternative criteria having the second meaning.

10. The system of claim 9, wherein analyzing the plurality of documents to determine the confidence value for the respective criterion comprises determining a relevancy of the respective criterion with respect to each of the set of documents.

11. The system of claim 9, wherein the information of the first clinical trial further includes a domain of the first clinical trial, and wherein identifying the set of documents is further based on the domain of the first clinical trial.

12. The system of claim 9, the method further comprising:
generating the plurality of alternative criteria for the second criterion, wherein each of the plurality of alternative criteria has a single respective meaning; and
presenting the plurality of alternative criteria to the user.

13. The system of claim 9, the method further comprising:
generating a new criteria based on analyzing the set of documents, wherein the new criteria is not included in the plurality of criteria; and
presenting the new criteria to the user.

14. The system of claim 9, the method further comprising:
estimating a first number of patients that are eligible for the first clinical trial based on the plurality of criteria;
estimating a second number of patients that are eligible for the first clinical trial based on all of the plurality of criteria other than the first criterion; and
presenting the first number of patients and the second number of patients to the user.

15. The system of claim 9, wherein determining the confidence value for the first criterion comprises determining that a second criterion contradicts the first criterion.

16. The system of claim 9, further comprising presenting an explanation of the confidence value for the first criterion to the user.

17. A non-transitory computer readable medium comprising instructions, which when executed by a processor of a computing device, cause the computing device to perform a method, the method comprising:
generating an index for a corpus of literature, wherein the index comprises a vector space comprising a plurality of vectors associated with documents clustered based on similarities, and wherein the index is generated by:
preprocessing a first document of a plurality of documents using one or more natural language processing (NLP) algorithms, comprising removing stop words, performing tokenization, performing stemming, removing non-English words, and removing punctuation;
identifying a first instance of a predefined section of the first document based on metadata tags associated with the first document;
generating a first vector based on characteristics of the first document, comprising:
parsing only the first instance of the predefined section; and
refraining from parsing at least one other section of the first document;
generating a second vector based on characteristics of a second document, comprising:
searching for a second instance of the predefined section of the second document; and
in response to determining the second predefined section cannot be found in the second document, parsing the second document; and
clustering the first and second documents based on a similarity between the first and second vectors;
receiving information of a first clinical trial that is being drafted, wherein the information includes a plurality of criteria for the first clinical trial and a title of the first clinical trial;
generating a first vector for the title of the first clinical trial;
identifying, based on the index for the corpus of literature, a set of documents that are related to the first clinical trial, based on the first vector and the respective vectors of the plurality of documents in the corpus of literature;
generating, for each respective criterion of the plurality of criteria, a respective confidence value by providing the respective criterion to a machine learning model trained to output confidence values based on input criteria, wherein the respective confidence value is based at least in part on:
a respective frequency of the respective criterion in the set of documents, wherein a first document in the set of documents is given increased weight based on determining that the first document is associated with a successful trial of a therapy that obtained regulatory approval;
comparing each respective confidence value with a confidence threshold, wherein the confidence threshold is selected based on scaling used for the confidence values;
upon determining that a first criterion of the plurality of criteria has a first confidence value below the confidence threshold, prompting a user to verify the first criterion; and
upon receiving, from the user, verification that the first criterion is correct, updating the machine learning model to produce relatively higher confidence values for criteria that are similar to the first criterion;
determining that a second criterion of the plurality of criteria has two potential meanings, comprising:
parsing the second criterion with a first natural language processing (NLP) model to generate a first meaning; and
parsing the second criterion with a second NLP model to generate a second meaning distinct from the first meaning; and
generating a plurality of alternative criteria for the second criterion, the plurality of alternative criteria comprising a first alternative criteria having the first meaning and a second alternative criteria having the second meaning.

18. The non-transitory computer readable medium of claim 17, the method further comprising:
generating a new criteria based on analyzing the set of documents, wherein the new criteria is not included in the plurality of criteria; and
presenting the new criteria to the user.

* * * * *